(12) United States Patent
Tamaru et al.

(10) Patent No.: US 10,441,767 B2
(45) Date of Patent: Oct. 15, 2019

(54) JIG FOR MICRONEEDLE ARRAY PLACEMENT AND MICRONEEDLE ARRAY DEVICE

(75) Inventors: Takuya Tamaru, Hamamatsu (JP); Isamu Nonaka, Hamamatsu (JP); Yuko Wada, Hamamatsu (JP)

(73) Assignee: ASTI CORPORATION, Hamamatsu-Shi, Shizuoka (JP)

( * ) Notice: Subject to any disclaimer, the term of this patent is extended or adjusted under 35 U.S.C. 154(b) by 1250 days.

(21) Appl. No.: 13/880,714

(22) PCT Filed: Oct. 27, 2011

(86) PCT No.: PCT/JP2011/074829
§ 371 (c)(1),
(2), (4) Date: Apr. 19, 2013

(87) PCT Pub. No.: WO2012/057270
PCT Pub. Date: May 3, 2012

(65) Prior Publication Data
US 2013/0218084 A1    Aug. 22, 2013

(30) Foreign Application Priority Data
Oct. 27, 2010  (JP) ................................ 2010-240245

(51) Int. Cl.
*A61M 37/00*    (2006.01)

(52) U.S. Cl.
CPC .............................. *A61M 37/0015* (2013.01)

(58) Field of Classification Search
CPC ...... A61M 37/0015; A61M 2037/0023; A61M 2037/003; A61M 2037/0053; A61M 5/427; A61M 5/14248
See application file for complete search history.

(56) References Cited

U.S. PATENT DOCUMENTS 4,601,707 A * 7/1986 Albisser ............ A61M 5/14244
604/131
6,132,755 A * 10/2000 Eicher ................. A61M 31/002
424/427

(Continued)

FOREIGN PATENT DOCUMENTS

JP       11-509123 A    8/1999
JP     2001-149485 A    6/2001

(Continued)

OTHER PUBLICATIONS

International Search Report in PCT/JP2011/074829 dated Jan. 17, 2012 (English Translation Thereof).

*Primary Examiner* — Nathan R Price
*Assistant Examiner* — Weng Lee
(74) *Attorney, Agent, or Firm* — McGinn I.P. Law Group, PLLC.

(57) ABSTRACT

The invention relates to a jig for microneedle array placement that is provided with a main jig body with through holes through which the microneedles of the microneedle array will pass and a guiding part that guides the microneedle array to be incorporated into the main jig body and leads the microneedles into the through holes, and a microneedle array device using the jig for microneedle array placement. The invention prevents the deformation of the skin surface during puncture and allows penetration of the microneedles to the prescribed depth under the skin.

18 Claims, 22 Drawing Sheets

(56) References Cited

U.S. PATENT DOCUMENTS

| | | | |
|---|---|---|---|
| 6,607,513 B1 | 8/2003 | Down et al. | |
| 6,623,457 B1 | 9/2003 | Rosenberg | |
| 6,780,171 B2 * | 8/2004 | Gabel | A61M 5/14248 604/181 |
| 2002/0138049 A1 | 9/2002 | Allen et al. | |
| 2004/0162521 A1 * | 8/2004 | Bengtsson | A61B 5/14532 604/136 |
| 2004/0176732 A1 * | 9/2004 | Frazier | A61M 37/0015 604/345 |
| 2006/0100584 A1 | 5/2006 | Olejnik et al. | |
| 2007/0098773 A1 | 5/2007 | Olejnik et al. | |
| 2007/0098774 A1 | 5/2007 | Olejnik et al. | |
| 2008/0221524 A1 | 9/2008 | Olejnik et al. | |
| 2010/0121271 A1 * | 5/2010 | Perriere | A61M 5/14248 604/110 |
| 2011/0092883 A1 * | 4/2011 | Uchiyama | A61M 37/0015 604/21 |

FOREIGN PATENT DOCUMENTS

| | | |
|---|---|---|
| JP | 2002-517300 A | 6/2002 |
| JP | 2003-535625 A | 12/2003 |
| JP | 2008-509723 A | 4/2008 |

\* cited by examiner

JIG FOR MICRONEEDLE ARRAY PLACEMENT AND MICRONEEDLE ARRAY DEVICE

TECHNICAL FIELD

The present invention relates to a jig for microneedle array placement and a microneedle array device, and in particular, by using the jig for microneedle array placement, the deformation of the skin surface during puncture is prevented, and the microneedles can be penetrated to the prescribed depth under the skin securely.

BACKGROUND ART

There are some prior arts with regard to a microneedle or a microneedle array, for example as disclosed in Patent Document 1 and Patent Document 2. These disclosures have the structure in which the microneedle or microneedle array is provided perpendicular to a base plate. Further according to the prior art, for example as shown in Patent Document 2, the placement of microneedle or microneedle array to the skin surface is carried out by an adhering part, that is provided on the base plate separately, in a part other than for the part in which the microneedle or the microneedle array is provided. In addition, even in this case, the adhering part serves its function after puncture by microneedle.

PRIOR ART DOCUMENTS

Patent Documents

Patent Document 1: Japanese Unexamined Patent Publication No. 2002-517300; and
Patent Document 2: Japanese Unexamined Patent Publication No. 2008-509723.

SUMMARY OF THE INVENTION

Problems to be Solved by Invention

The prior art as discussed above has the following problems:

According to the prior art, as shown in FIG. 22, a microneedle 301 punctures a skin surface 303 in a perpendicular direction, but at that time, the tip of the microneedle 301 deforms the skin surface 303, and consequently, the microneedle 301 cannot carry out the penetration to the prescribed depth under the skin.

Where the microneedles cannot be penetrated to the prescribed depth under the skin, if a medicinal solution is supplied to a medicinal solution flow channel 305 of the microneedle 301, the medicinal solution leaks out on the skin surface 303.

In this state, if the microneedle 301 is pushed further, the patient feels more pain.

By considering the pain relief of patient and the effective injection of medicinal solution, the appropriate depth of penetration is about 100-500 μm under the skin surface.

In the light of the problem as discussed above, it is an object of the present invention to provide a jig for microneedle array placement and a microneedle array device, in which, the deformation of the skin surface during puncture is prevented, and the microneedles can be penetrated to the prescribed depth under the skin.

Means to Solve the Problem

To achieve the objects mentioned above, according to Claim 1 of the present invention, there is a jig for microneedle array placement, comprising: a main jig body having through holes for penetration of microneedles of a microneedle array; and a guiding part for guiding said microneedle array incorporated in said main jig body, so that said microneedles are lead to said through holes.

According to Claim 2 of the present invention, with regard to the jig for microneedle array placement of Claim 1, the surface of said main jig body is provided with an adhering part.

According to Claim 3 of the present invention, with regard to the jig for microneedle array placement of Claim 2, said main jig body is provided with microneedle array holders for holding said microneedle array incorporated in said main jig body.

According to Claim 4 of the present invention, with regard to the jig for microneedle array placement of Claim 3, said microneedle array holders are latches placed to be opposing to each other in said main jig body.

According to Claim 5 of the present invention, with regard to the jig for microneedle array placement of Claim 4, said main jig body is provided with belt connecting holes for connecting fastening belts.

According to Claim 6 of the present invention, there is a microneedle array device comprising: the jig for microneedle array placement as claimed in any Claim among Claim 1 through Claim 5; and a microneedle array incorporated and fixed in said jig for microneedle array placement.

According to Claim 7 of the present invention, with regard to the microneedle array device of Claim 6, said microneedle array comprises microneedle units held by a needle holder, in a state of being sandwiched and fixed between an upper case, and a lower case having a medicinal solution inlet.

According to Claim 8 of the present invention, with regard to the microneedle array device of Claim 7, said upper case has grooves formed for guiding the both ends of said microneedle units.

According to Claim 9 of the present invention, with regard to the microneedle array device of Claim 8, said microneedle unit is provided with flow channel bosses, and is fixed by inserting said flow channel bosses into through holes formed in said needle holder.

And according to Claim 10 of the present invention, with regard to the microneedle array device of Claim 9, said lower case is provided with a plurality of projections for preventing deformation of said needle holder, and spaces between said plurality of projections serve as flow channels.

Effect of the Invention

As discussed above, the jig for microneedle array placement as claimed in Claim 1 of the present invention is provided with the main jig body having through holes for penetration of microneedles of the microneedle array, and the guiding part for guiding the microneedle array incorporated in the main jig body, so that the microneedles are lead to the through holes. With this structure, the main jig body fixes the skin surface, whereby the deformation of the skin surface during puncturing by the microneedles is prevented, and the microneedles can be penetrated to the prescribed depth under the skin securely. In addition, because of the guiding part, the microneedles can be guided to the through holes securely.

According to the jig for microneedle array placement of Claim 2, with regard to the jig for microneedle array placement of Claim 1, the surface of the main jig body is provided with the adhering part. With this structure, the adhering part can fix the jig for microneedle array placement on the skin surface. The adhering part can also keep the skin surface itself as a flat surface, and the improvement of the above is accomplished.

According to the jig for microneedle array placement of Claim 3, with regard to the jig for microneedle array placement of Claim 2, the main jig body is provided with the microneedle array holders for holding the microneedle array incorporated in the main jig body. With this structure, the jig for microneedle array placement can hold and fix the microneedle array securely.

According to the jig for microneedle array placement of Claim 4, with regard to the jig for microneedle array placement of Claim 3, the microneedle array holders are the latches placed to be opposing to each other in the main jig body. With this structure, the above effect can be accomplished more securely.

According to the jig for microneedle array placement of Claim 5, with regard to the jig for microneedle array placement of Claim 4, the main jig body is provided with the belt connecting holes for connecting the fastening belts. With this structure, the fixing with the use of belts can be carried out.

The microneedle array device of Claim 6 is provided with the jig for microneedle array placement as claimed in any Claim among Claim 1 through Claim 5, and the microneedle array incorporated and fixed in the jig for microneedle array placement. With this structure having the jig for microneedle array placement, the deformation of the skin surface during puncture by the microneedles is prevented, and the microneedles provided in the microneedle array can be penetrated to the prescribed depth under the skin securely, and also the leak out of the medicinal solution on the skin surface is prevented with the simultaneous effect of relieving patient's pain.

According to the microneedle array device of Claim 7, with regard to the microneedle array device of Claim 6, the microneedle array comprises the microneedle units held by the needle holder, in a state of being sandwiched and fixed between the upper case, and the lower case having the medicinal solution inlet. With this structure, the improvement of sealing performance is accomplished, the needless retention of medicinal solution is prevented, and the easy assembly is accomplished.

According to the microneedle array device of Claim 8, with regard to the microneedle array device of Claim 7, the upper case has the grooves formed for guiding the both ends of the microneedle units. With this structure, the positioning of the microneedle units can be facilitated.

According to the microneedle array device of Claim 9, with regard to the microneedle array device of Claim 8, the microneedle unit is provided with the flow channel bosses, and is fixed by inserting the flow channel bosses into through holes formed in the needle holder. With this structure, the microneedle units can be held securely and easily.

And according to the microneedle array device of Claim 10, with regard to the microneedle array device of Claim 9, the lower case is provided with a plurality of projections for preventing deformation of the needle holder, and spaces between the projections serve as the flow channels. With this structure, by securing the required flow channels, the deformation of the needle holder can be prevented.

BRIEF DESCRIPTION OF DRAWINGS

FIG. 16 Views according to the second embodiment of the present invention, in which FIG. 16(a) is an expanded partial perspective view showing a part of a contact surface side of a main-needle side divisional element, and FIG. 16(b) is an expanded partial perspective view showing a part of a contact surface aide of a sub-needle side divisional element.

FIG. 17 Views according to the second embodiment of the present invention, in which FIG. 17(a) is an exploded perspective view showing a jig for microneedle array placement and a microneedle array at an initial state of using, FIG. 17(b) is a perspective view showing a state before puncture, in which the microneedle array is mounted to the jig for microneedle array placement to be used, and FIG. 17(c) is an exploded perspective view after puncture, in which the microneedle array is mounted to the jig for microneedle array placement to be used.

FIG. 20 Views according to the third embodiment of the present invention, in which FIG. 20(a) is an exploded sectional view of the microneedle array device, and FIG. 20(b) is a sectional view of the microneedle array device.

FIG. 21 Views according to the third embodiment of the present invention, in which FIG. 21(a) is a perspective view showing a state of puncture by the microneedle array device, and FIG. 21(b) is a sectional view as viewed from the line b-b of FIG. 21(a).

BEST MODE FOR CARRYING OUT THE INVENTION

Figure 1:
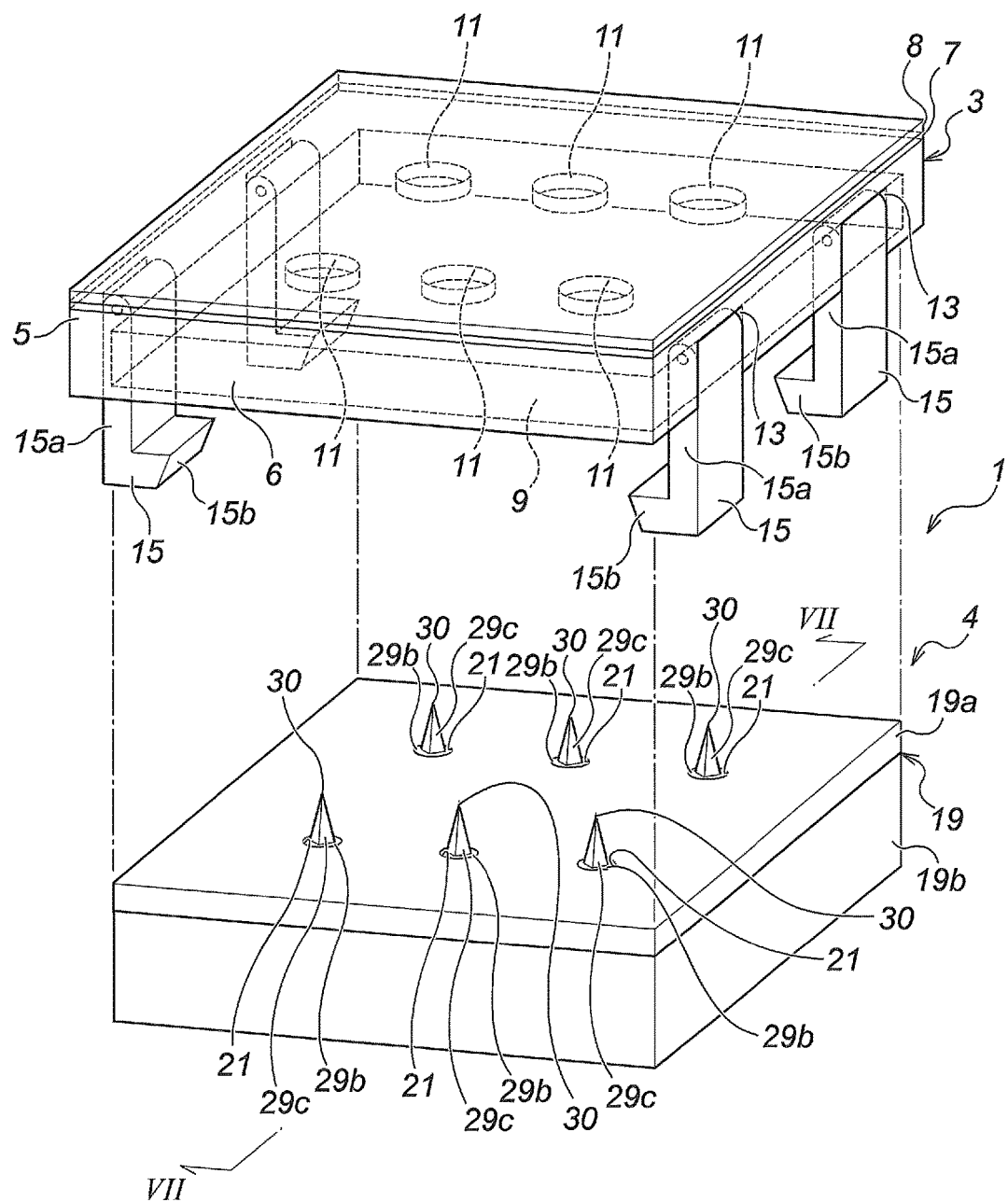
FIG. 1 An exploded perspective view showing a microneedle array device according to a first embodiment of the present invention.
Figure 2:
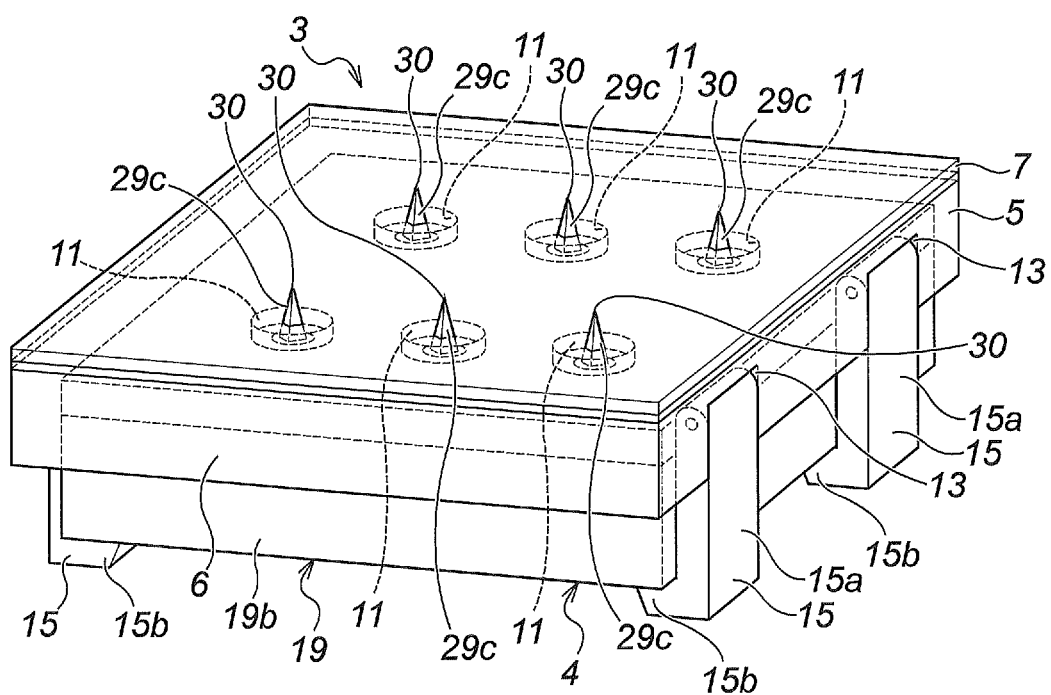
FIG. 2 A perspective view showing the microneedle device according to the first embodiment of the present invention.

Now a first embodiment of the present invention will be discussed with reference to FIG. 1 through FIG. 8. As illustrated in FIG. 1, a microneedle array device 1 according to the present invention is provided with a jig for microneedle array placement 3, and a microneedle array 4 capable of being attached to and detached from the jig for microneedle array placement 3.

The structure thereof will be explained in detail as below.

The structure of the jig for microneedle array placement 3 will be discussed first.

The jig for microneedle array placement 3 is provided with a main jig body 5 made of a panel substantially in a square shape, an adhering part 7 comprising an adhesive applied thoroughly to one side (the upper side of FIG. 1) of the main jig body 5, and a guiding part 6 formed on the outer peripheral surface of the other side (the lower surface of FIG. 1) of the main jig body 5 and extending in the downward direction.

A release paper 8 is sticking to the whole opposite side (the upper side of FIG. 1) of the adhering part 7 of the main jig body 5, capable of being released. The release paper 8 protects the adhering part 7 not to stick to any other structural member carelessly.

The main jig body 5 and the guiding part 6 form a hollow part 9, having an opening in the lower part as shown in FIG. 1. The main jig body 5 is also provided with a plurality of (in the present embodiment, six) penetrating through holes 11, 11, 11, 11, 11, 11. The through holes 11, 11, 11, 11, 11, 11 are communicating with the hollow part 9. With reference to the through holes 11, 11, 11, 11, 11, 11, the respective upper opening portions as shown in FIG. 1 are closed by the adhering part 7.

The guiding part 6 has two pairs of cutaway parts 13 formed both on the right and left sides of FIG. 1. Each of the cutaway parts 13 has a latch 15 serving as a microneedle array holder, attached to be rotatable in the right and left directions of FIG. 1. The latch 15 is composed of an arm 15a attached to the guiding part 6, and a hook 15b formed at the elongating end of the arm 15a.

As explained above, the detachable microneedle array 4 is attached to the microneedle array device 3 as discussed above. The detailed structure of the microneedle array 4 will now be discussed.

Figure 3:
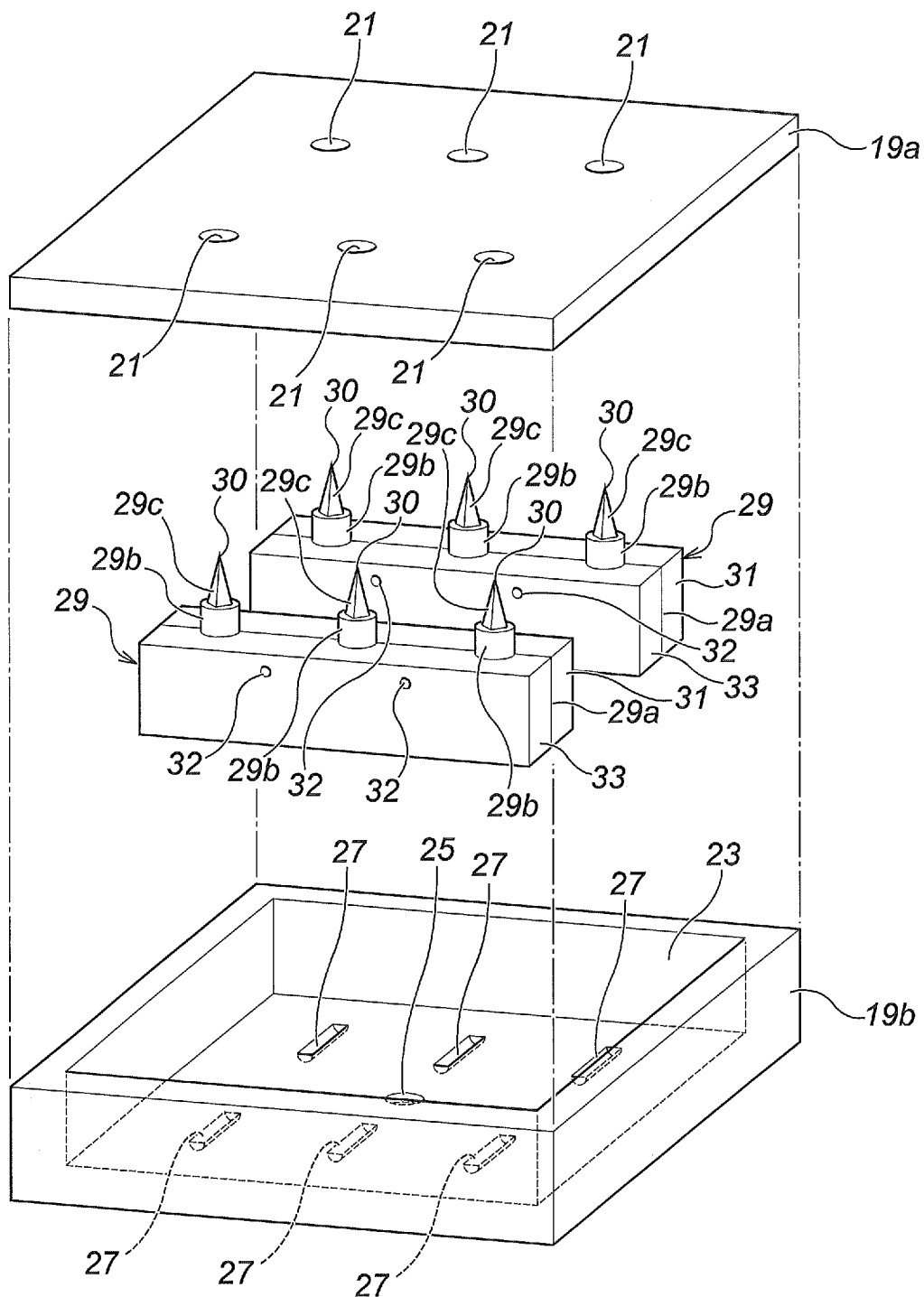
FIG. 3 An exploded perspective view showing a microneedle array used for the microneedle array device according to the first embodiment of the present invention.

There is a case 19, and as illustrated in FIG. 1 and FIG. 3, the case 19 is composed of an upper case 19a and a lower case 19b. Also as illustrated in FIG. 3, the upper case 19a has a plurality of (in the present embodiment, six) penetrating through holes 21, 21, 21, 21, 21, 21. On the other hand, as illustrated in FIG. 3, the lower case 19b has a hollow part 23 having an opening in the upper part as shown in FIG. 3, and a medicinal solution inlet 25 is formed at the center of the bottom surface of the hollow part 23 (on the inner surface as shown in the lower part of FIG. 3). Further, the inner surface of the hollow part 23 as shown in the lower part of FIG. 3 has a plurality of (in the present embodiment, six) medicinal solution distribution grooves 27, 27, 27, 27, 27, 27 formed therein.

As illustrated in FIG. 3, two microneedle units 29, 29 are placed in the inner part of the case 19. The microneedle unit 29 is made of resin material, composed of a main body 29a substantially in a cuboid shape, and base parts 29b, 29b, 29b, each of which being substantially in a cylindrical shape and formed to be projecting in a perpendicular direction from the upper surface of the main body 29a as shown in FIG. 3, and microneedles 29c, 29c, 29c, each of which being in a quadrangular pyramid shape and formed to be projecting in a perpendicular direction from the upper surface of each of the base parts 29b as shown in FIG. 3.

Figure 4:
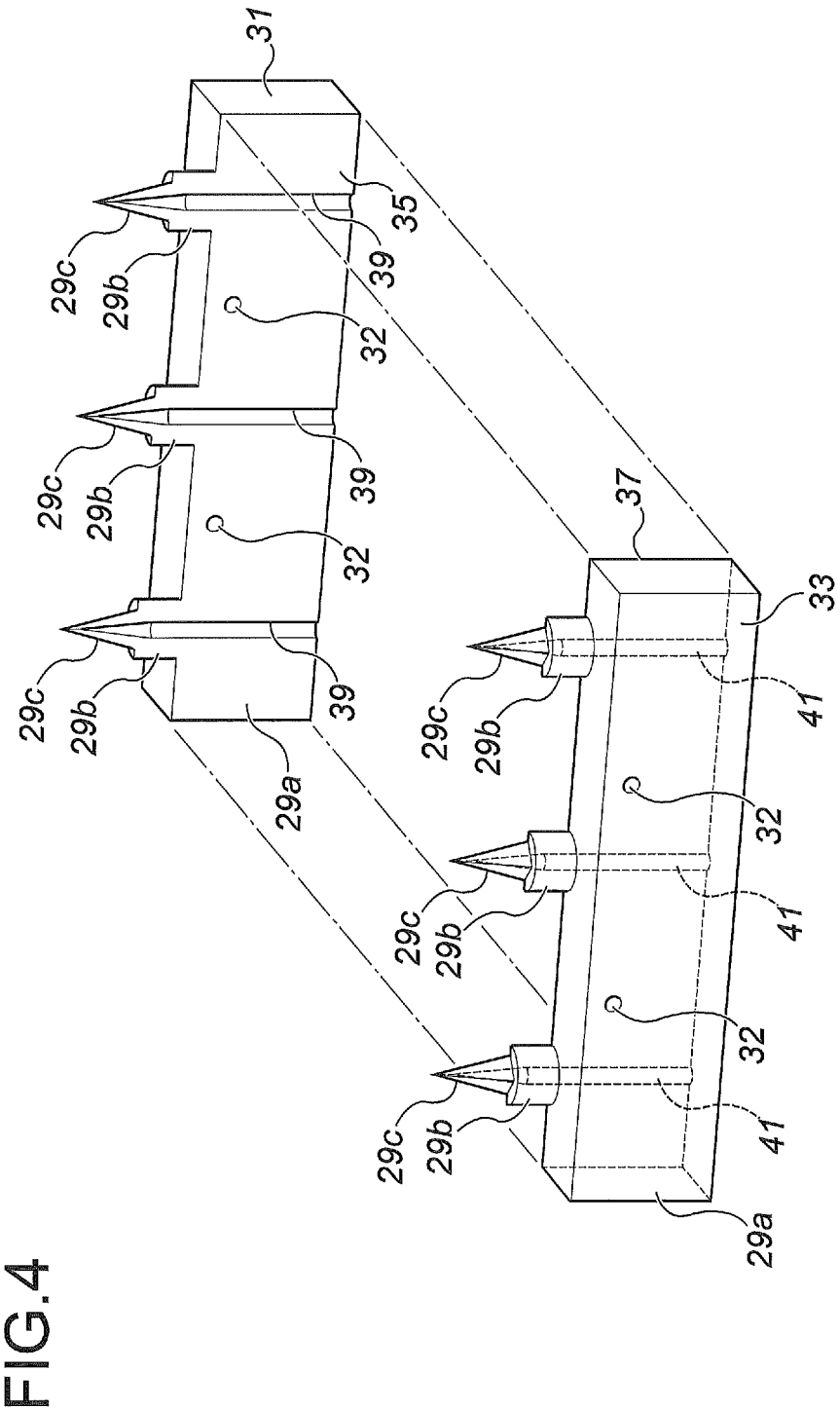
FIG. 4 An exploded perspective view showing a microneedle unit serving as a structural element of the microneedle array used for the microneedle array device according to the first embodiment of the present invention.
Figure 8:
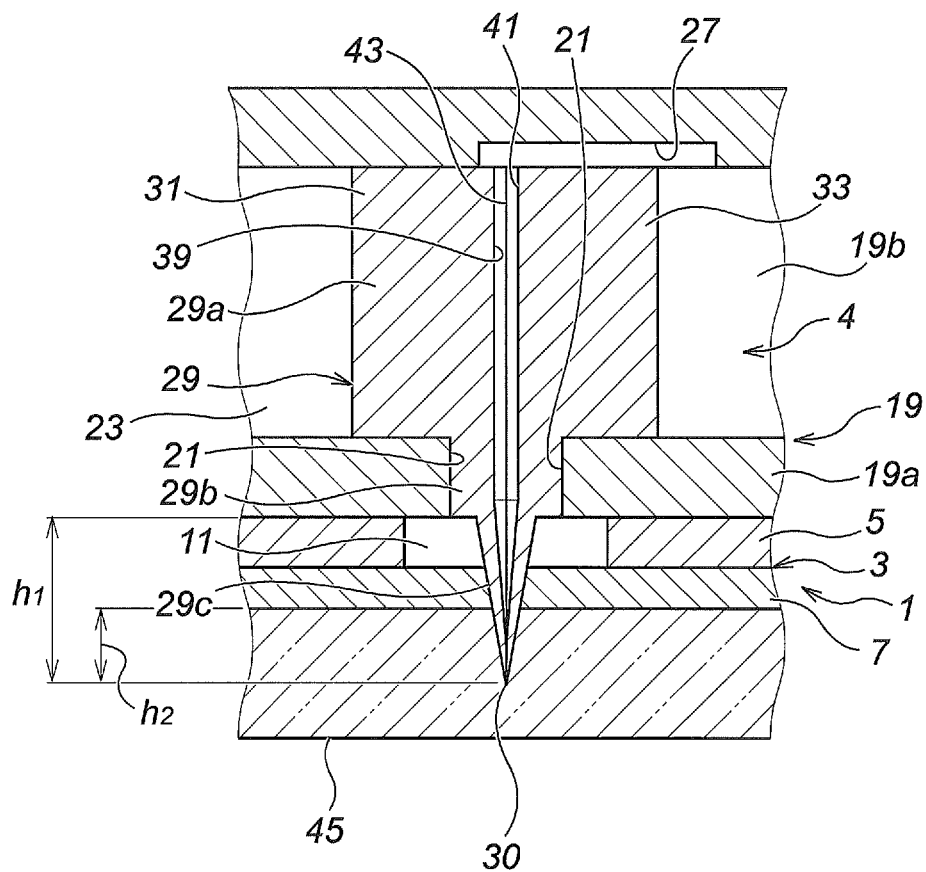
FIG. 8 A partial sectional view according to the first embodiment of the present invention, showing a state that the microneedle array has been attached to the jig for microneedle array placement, and the microneedle punctures the skin surface.

As illustrated in FIG. 4, the microneedle unit 29 can be divided into two elements, namely composed of two divisional elements 31, 33. Each of these divisional elements 31, 33 has a shape that the microneedle unit 29 is evenly divided into two portions in the perpendicular direction (up-down direction of FIG. 3). The divisional element 31 has a contact surface 35 facing to the divisional element 33, in which grooves 39, 39, 39 are formed as shown in FIG. 4. Also, the divisional element 33 has a contact surface 37 facing to the divisional element 31, in which grooves 41, 41, 41 are formed. When the microneedle unit 29 is formed by the divisional element 31 and the divisional element 33 as discussed above, the grooves 39 and the grooves 41 serve as medicinal solution flow channels 43 (as shown in FIG. 8).

The medicinal solution flow channel 43 elongates from the portion in the vicinity of the microneedle 29c to the bottom surface of the main body 29a of the microneedle unit 29 (the lower surface as shown in FIG. 3), and has an opening at the bottom surface of the main body 29a of the microneedle unit 29 (the lower surface as shown in FIG. 3).

The microneedle unit 29 is obtained, by adhering and fixing of the pair of divisional element 31 and divisional element 33, via the contact surfaces 35, 37 as discussed above.

However, the tip of the microneedle 29c is free from adhesion, and serves as a medicinal solution outlet 30.

As illustrated in FIG. 3 and FIG. 4, the divisional element and the divisional element 33 are provided, respectively, with penetrating through holes 32, 32 for the purpose of positioning. When the microneedle unit 29 is formed by adhering the divisional element 31 to the divisional element 33, unillustrated pins are penetrated through the positioning through holes 32, 32 for the purpose of positioning, whereby the adhesion of the divisional element 31 to the divisional element 33 can be carried out precisely.

As illustrated in FIG. 8, the length of the microneedle 29c projecting from the surface of the adhering part 7 of the jig for microneedle array placement 3 (the length of penetration into a skin surface 45 of patient: $h_2$) must be adjusted so that the medicinal solution outlet 30 of the microneedle 29c may be penetrated sufficiently into the skin surface 45, and that the administration of medicinal solution can be carried out efficiently by preventing the leak out of the medicinal solution on the skin surface 45, and that the patient may be relieved from any pain. Therefore the height of the microneedle 29c (the length in the up-down direction of FIG. 7: $h_1$) must be set appropriately by considering that purpose.

Figure 7:
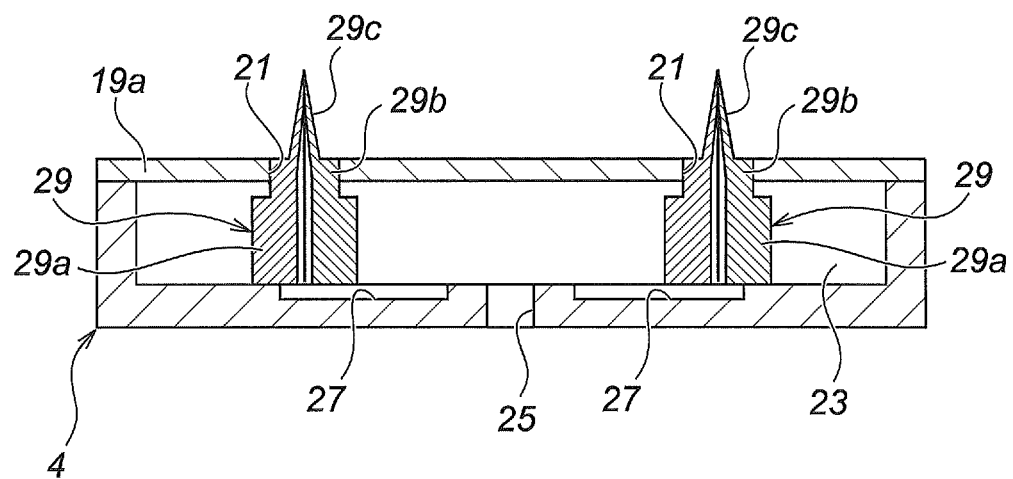
FIG. 7 A sectional view according to the first embodiment of the present invention, as viewed from the line VII-VII of FIG. 1.

As illustrated in FIG. 7, the microneedles 29c, 29c, 29c of the microneedle unit 29 penetrate, respectively, through the through holes 21, 21, 21 of the upper case 19a, and the base parts 29b, 29b, 29b of the microneedle unit 29 become in engagement, respectively, with the inner portions of the through holes 21, 21, 21.

As illustrated in FIG. 7 and FIG. 8, where the microneedle unit 29 is placed in the inner portion of the lower case 19b, the microneedle unit 29 is positioned above the medicinal solution distribution grooves 27, and in such a state, a part of the medicinal solution distribution groove 27 is positioned out of the microneedle unit 29. Accordingly, the medicinal solution injected into a space 23 via the medicinal solution inlet 25 flows into the inner portion of each of the microneedle units 29 via the medicinal solution distribution grooves 27, respectively.

The function of the present embodiment will now be discussed with reference to the structure as explained above.

Figure 5:
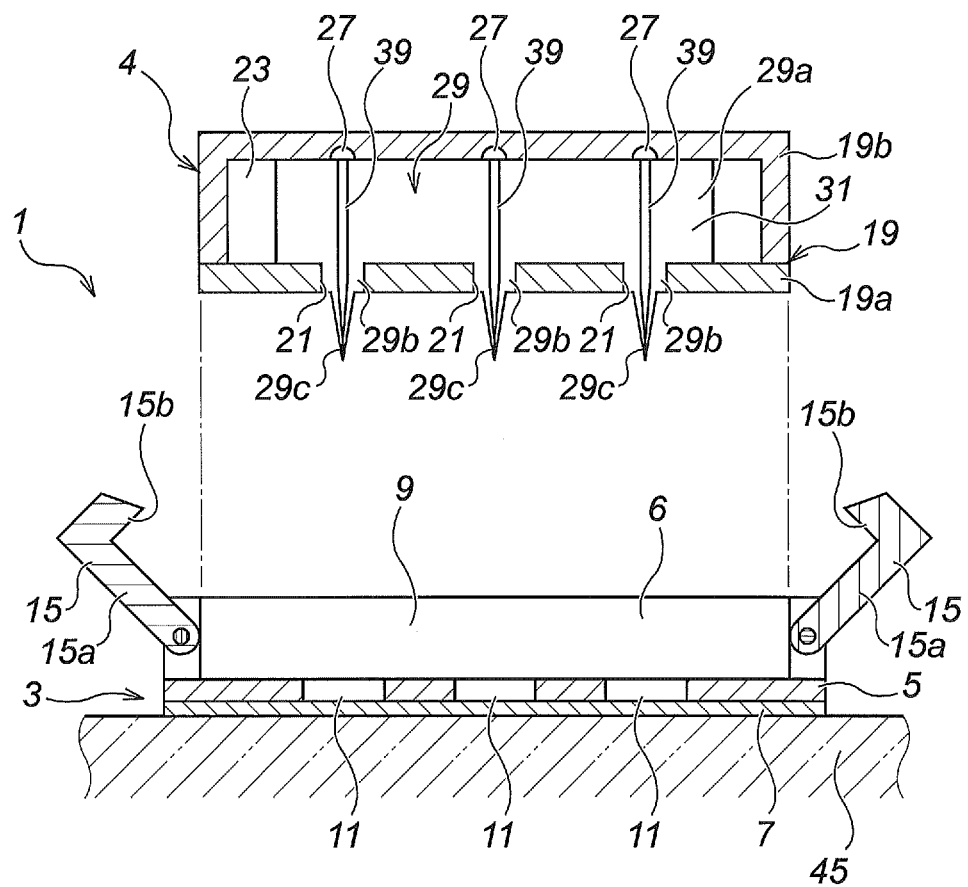
FIG. 5 A sectional view according to the first embodiment of the present invention, showing a state that the microneedle array is to be attached to a jig for microneedle array placement adhered to a skin surface.

First, the release paper 8 is released from the jig for microneedle array placement 3, whereby the adhering part 7 is exposed. Thereafter, as illustrated in FIG. 5, a surface of the jig for microneedle array placement 3 on the side of the adhering part 7 is pressed against the skin surface 45 to be adhered to with and fixed on the skin surface 45. Thus the skin surface 45 is fixed in a flat-surface state, and the expanding or shrinking thereof is prohibited.

Thereafter, as illustrated in FIG. 5, the microneedle array 4 is inserted in and engaged with the hollow part 9 of the jig for microneedle array placement 3 attached to the skin surface 45. At that time, the microneedle array 4 is guided by inner surfaces of the guiding part 6. Thus the microneedles 29c of the microneedle array 4 penetrate, respectively, into the through holes 11 of the main jig body 5.

Figure 6:
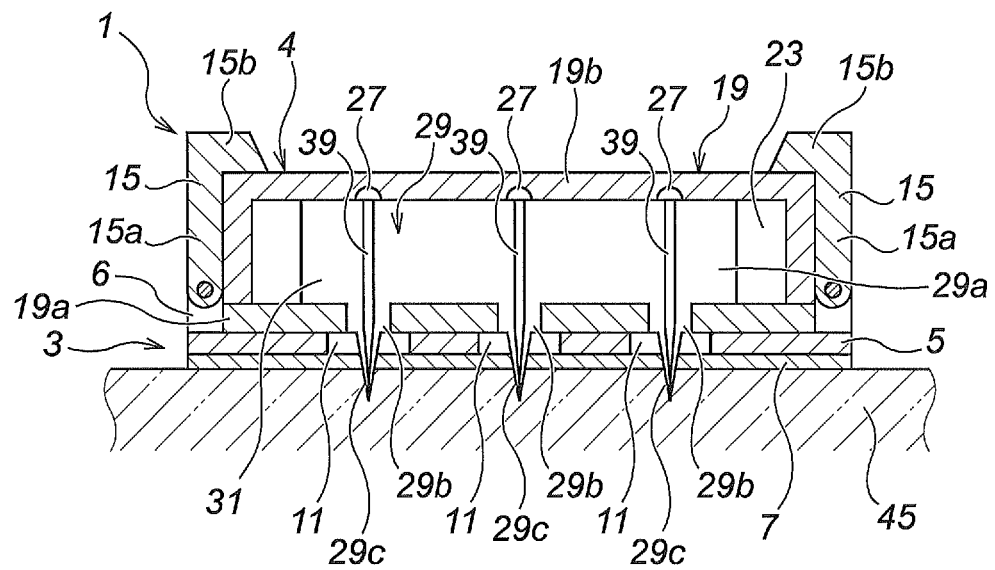
FIG. 6 A sectional view according to the first embodiment of the present invention, showing a state that the microneedle array has been attached to the jig for microneedle array placement, and the microneedles puncture the skin surface.
Figure 22:
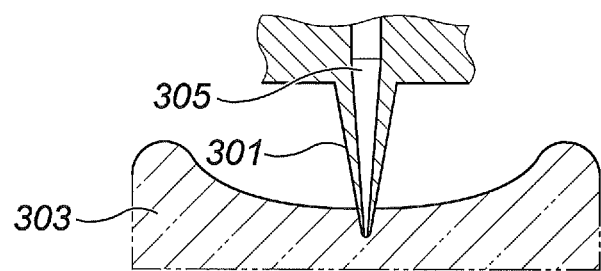
FIG. 22 A sectional view showing a prior art, in which a microneedle punctures a skin surface in a perpendicular direction.

As illustrated in FIG. 6, when the microneedle array 4 in a state of being engaged with the hollow part 9 is pushed further, each of the microneedles 29c breaks through the adhering part 7, and penetrates into the skin surface 45. In this state, as discussed above, since the skin surface 45 is fixed by the adhering part 7, the deformation of the skin surface 45 is prohibited (according to the prior art, as illustrated in FIG. 22, the skin surface 303 is deformed). Accordingly, as illustrated in FIG. 8, the flat-surface state of skin surface 45 is maintained by the adhering part 7, and the microneedles 29c penetrate into the skin surface 45.

Thereafter, the four latches 15 are rotated so that the hooks 15b are engaged with the reverse side (the upper surface as shown in FIG. 6) of the microneedle array 17. Accordingly, as illustrated in FIG. 6, the microneedle array 4 can be fixed in the jig for microneedle array placement 3.

Where necessary, the microneedle array 4 and the jig for microneedle array placement 3 may be fixed on the skin surface 45 by using unillustrated belts.

With this structure, the microneedle array 4 is attached to the skin surface 45 by using the jig for microneedle array placement 3, and the microneedles 29c of the microneedle array 4 can be penetrated into the skin surface 45 as discussed above.

Then unillustrated medicinal solution supply tube is connected to the medicinal solution inlet 25 of the microneedle array 4, and the medicinal solution is supplied to the microneedle array 4 by pump, etc., via the medicinal solution supply tube. The medicinal solution flows, from the medicinal solution inlet 25, into the inside portion of the hollow part 23 in the case 19 of the microneedle array 4, and passes through the each of the medicinal solution distribution grooves 27 formed in the bottom surface of the hollow part 23, and eventually flows into the medicinal solution flow channels 43 of the microneedle unit 29. The medicinal solution flowing into the medicinal solution flow channels 43 is then injected into the skin surface 45, from each of the medicinal solution outlets 30 at the tip of the microneedle 29c.

The present embodiment has the following effects.

First, the main body 5 of the jig for microneedle array placement 3 is pressed against the skin surface 45, whereby the skin surface 45 can be maintained in a flat-surface state. In particular, according to the present embodiment, since the adhering part 7 is provided on the surface of the main jig body 5, the effect of fixing the skin surface 45 in a flat-surface state can be accomplished more securely. As discussed above, since the skin surface 45 can be fixed in a flat-surface state, the deformation of the skin surface 45 during puncture can be prevented, and the microneedles 29c can be penetrated to the prescribed depth under the skin securely.

Further, since the jig for microneedle array placement 3 is provided with the guiding part 6, the microneedle array 4 can be attached to the jig for microneedle array placement 3 securely and easily.

Further, since the jig for microneedle array placement 3 has four latches 15, the microneedle array 4 can be fixed in the jig for microneedle array placement 3 securely, and the position of the microneedle array 4 against the skin surface 45 is also fixed securely.

In addition, since the penetration length of the microneedle 29c from the surface of the adhering part 7 of the jig for microneedle array placement 3 (that is the length of penetration into the skin surface 45) $h_2$ has been adjusted appropriately, the pain of the patient is relieved, and at the same time the injection of medicinal solution can be carried out efficiently.

Figure 9:
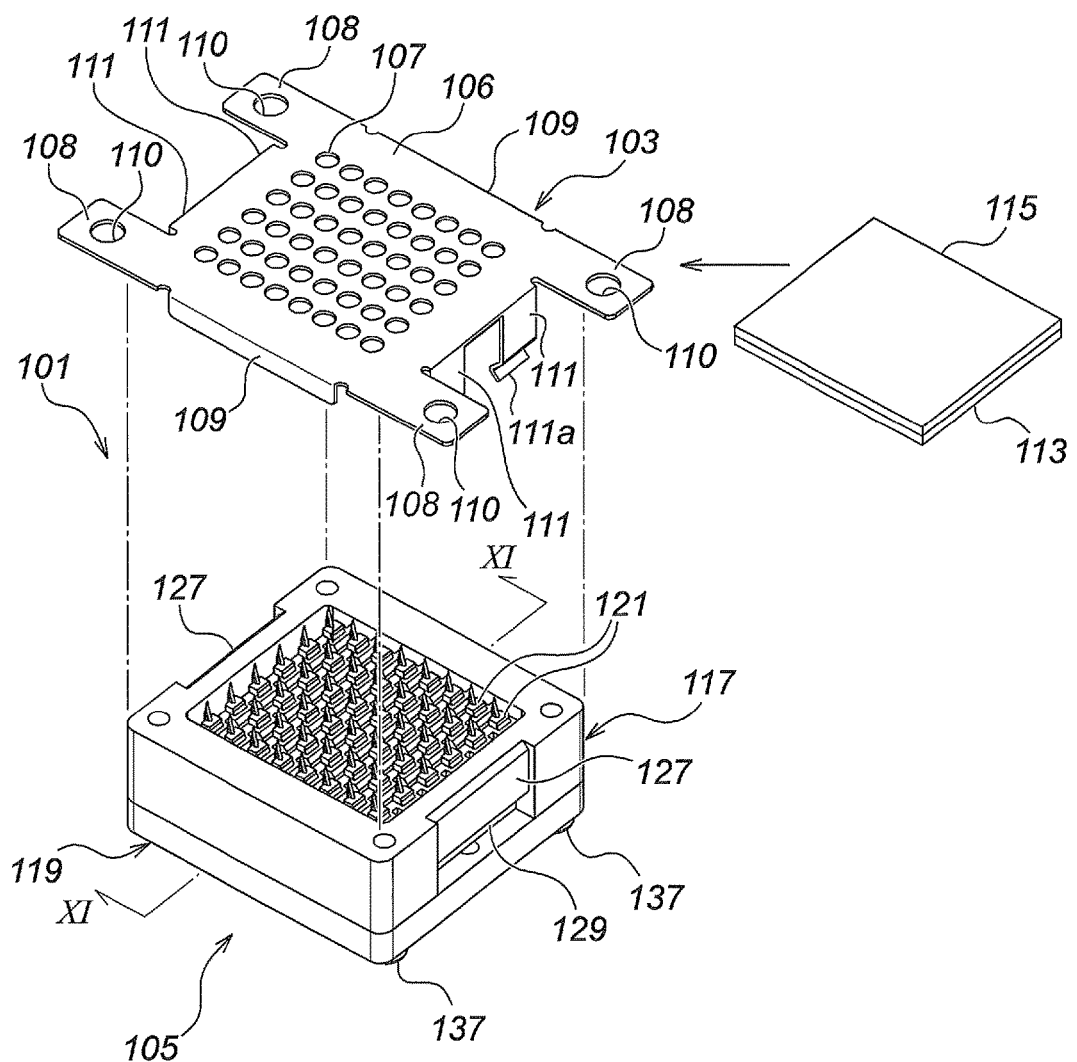
FIG. 9 An exploded perspective view of a microneedle array device according to a second embodiment of the present invention.

A second embodiment of the present invention will now be discussed with reference to FIG. 9 through FIG. 18. FIG. 9 is an exploded perspective view showing the structure of a microneedle array device 101 according to the second embodiment. The microneedle array device 101 is composed of a jig for microneedle array placement 103, and a detachable microneedle array 105 attached to the jig for microneedle array placement 103.

Figure 10:
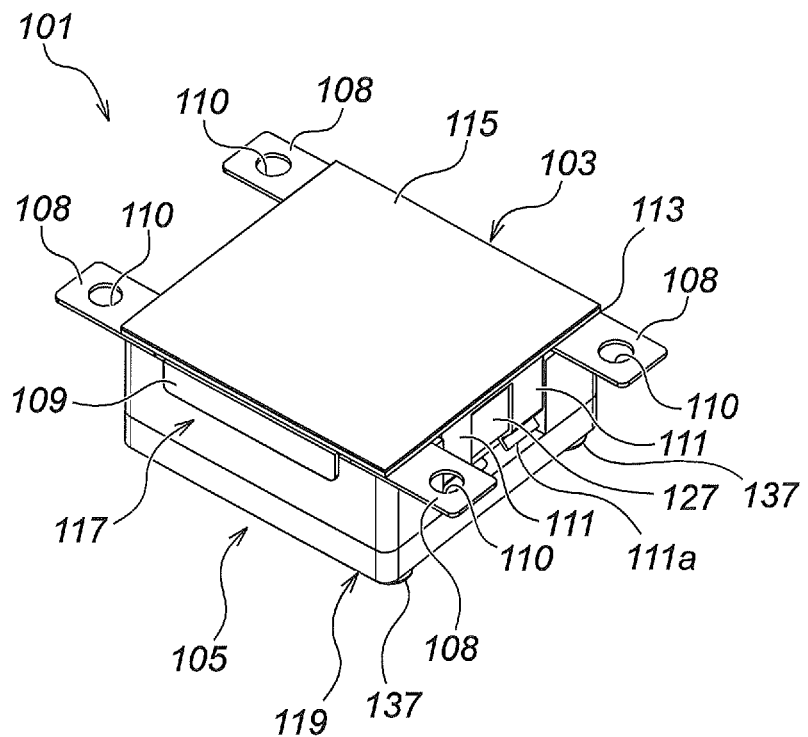
FIG. 10 A perspective view of the microneedle array device according to the second embodiment of the present invention.
Figure 11:
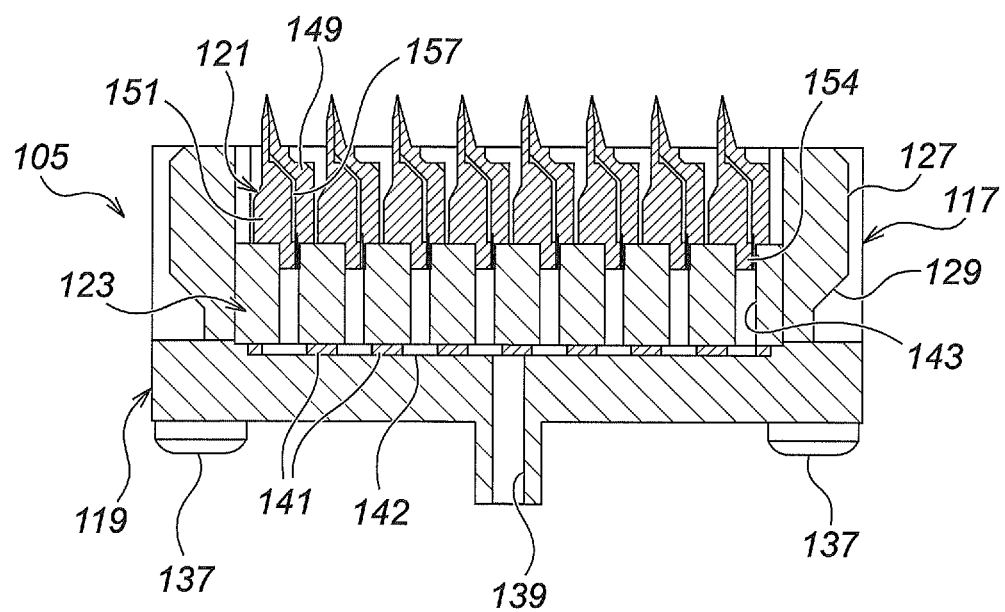
FIG. 11 A sectional view according to the second embodiment of the present invention, as viewed from the line XI-XI of FIG. 9.

The state in which the microneedle array 105 is attached to the jig for microneedle array placement 103 is shown in FIG. 10.

The structure of the jig for microneedle array placement 103 will be explained first. The jig for microneedle array placement 103 is made of metal material, formed by punching press. There is a main jig body 106. The main jig body 106 is in a flat-panel shape, having a plurality of (in the present embodiment, 6×8=48) through holes 107 formed therein. The main jig body 106 also has attachment support tips 108 formed to be projecting from the four corners, respectively. Each of these four attachment support tips 108 has a penetrating belt connecting hole 110, respectively. The four belt connecting holes 110 consist of two pairs, and can be fixed, for example on the arm, by putting through unillustrated belts.

The main jig body 106 has guiding side walls 109, 109, formed and bent on the two edges opposing to each other. The main jig body 106 also has two pairs of latches (microneedle array holders) 111, 111, formed respectively on the other two edges thereof opposing to each other. The latches 111, 111 are provided with holding hooks 111a, 111a, respectively, formed at the elongating ends thereof. The surface of the main jig body 106 is provided with an adhering part 113 by applying an adhesive thereto, and a release paper 115 is adhered to the surface of the adhering part 113.

Figure 12:
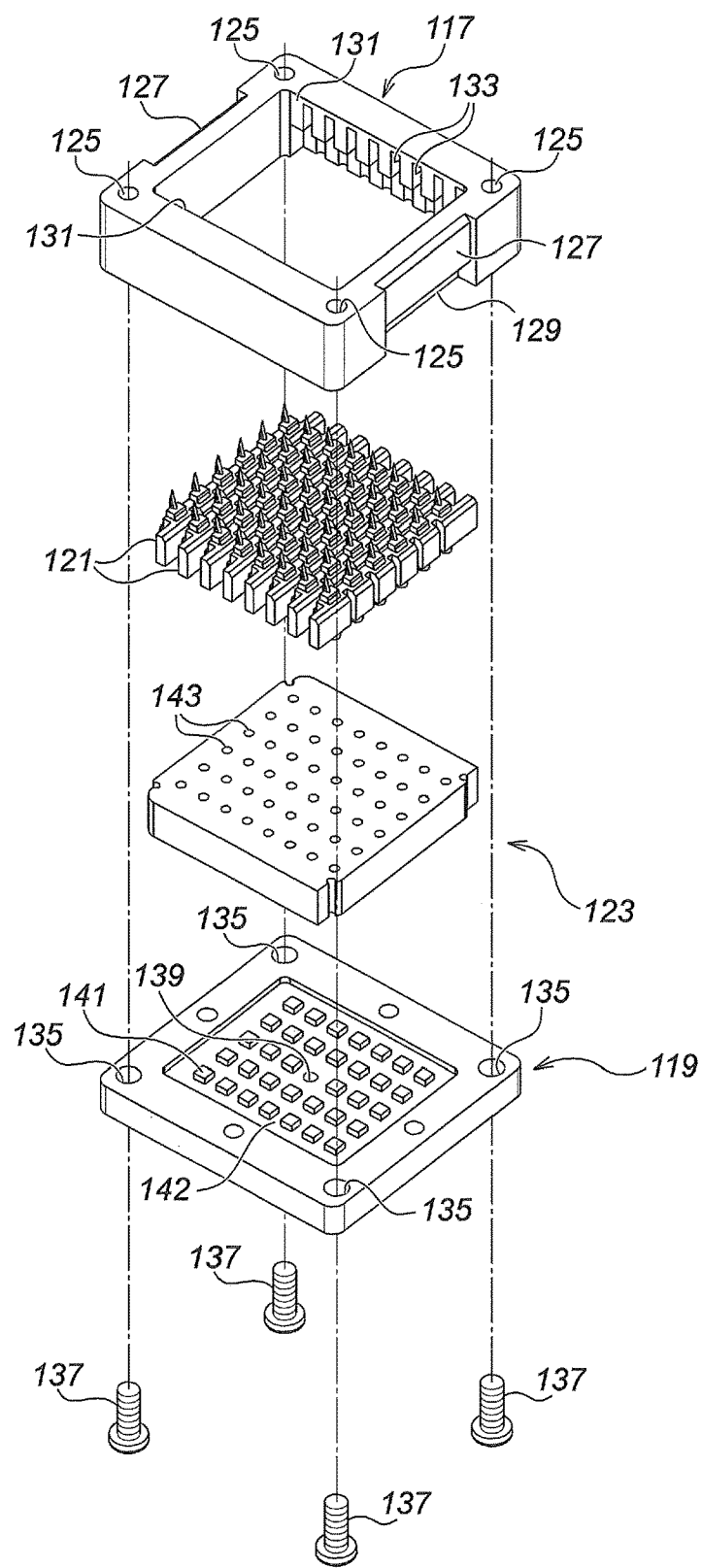
FIG. 12 An exploded perspective view of the microneedle array used for the microneedle array device according to the second embodiment of the present invention.

Now the structure of the microneedle array 105 will be explained. FIG. 12 illustrates the structure of the microneedle array 105, and FIG. 12 is an exploded perspective view of the microneedle array 105. There is an upper case 117 and also a lower case 119, and the microneedle array 105 has a structure in which a plurality of rows (in the present embodiment, eight rows) of microneedle units 121 are held by a needle holder 123 and sandwiched between the upper case 117 and the lower case 119.

The upper case 117 is in a quadrangular prism shape, of which body center is hollow, and has screw holes 125 at the four corners, respectively. There are engagement recesses 127, 127 formed on the two edges opposing to each other. These engagement recesses 127, 127 become in engagement with the latches 111, 111 as discussed above, respectively. The engagement recesses 127, 127 have stepped parts 129, 129 at the bottom end thereof, respectively, and the stepped parts 129, 129 become in engagement with holding hooks 111a, 111a of the latches 111, 111. With this structure, the upper case 117, and consequently the microneedle array 105, are fixed in the jig for microneedle array placement 103.

The upper case 117 has two inner surfaces 131, 131 opposing to each other, each of which having a plurality of rows (in the present embodiment, eight rows) of guide grooves 133, formed to be opposing to those on other side. Each of the pair of the guide grooves 133, 133, formed to be opposing to each other, guides each of the microneedle units 121, respectively.

FIG. 12 shows the inner surface 131 on one side and a plurality of the guide grooves 133.

Now the structure of the lower case 119 will be explained. The lower case 119 is substantially in a flat-panel shape, having through holes 135 penetrating in through the four corners, respectively. There are four fixing screws 134, passing through the four through holes 135 and become in engagement with four screw holes 125, respectively. Accordingly, a plurality of rows of the microneedle units 121, held by the needle holder 123, are sandwiched and fixed between the lower case 119 and the upper case 117. The lower case 119 has a medicinal solution inlet 139 formed at the center thereof, and a plurality of projections 141 are formed in order to prevent the deformation of the needle holder 123. The spaces between these projections 141 serve as medicinal solution distribution grooves 142.

The structure of the needle holder 123 will now be explained. The needle holder 123 is made of elastic material, for example silicone rubber. The needle holder 123 is substantially in a quadrangular prism shape, having a plurality of (in the present embodiment, 6×8=48) medicinal solution distribution holes 143 formed therein.

Figure 13:
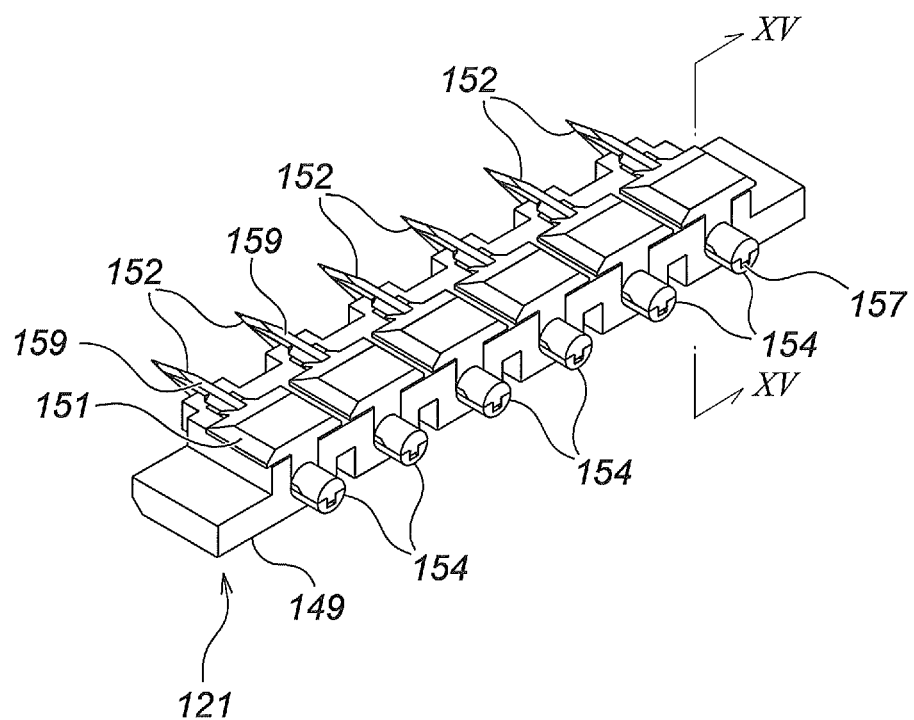
FIG. 13 A perspective view of a microneedle unit of the microneedle array used for the microneedle array device according to the second embodiment of the present invention.
Figure 14:
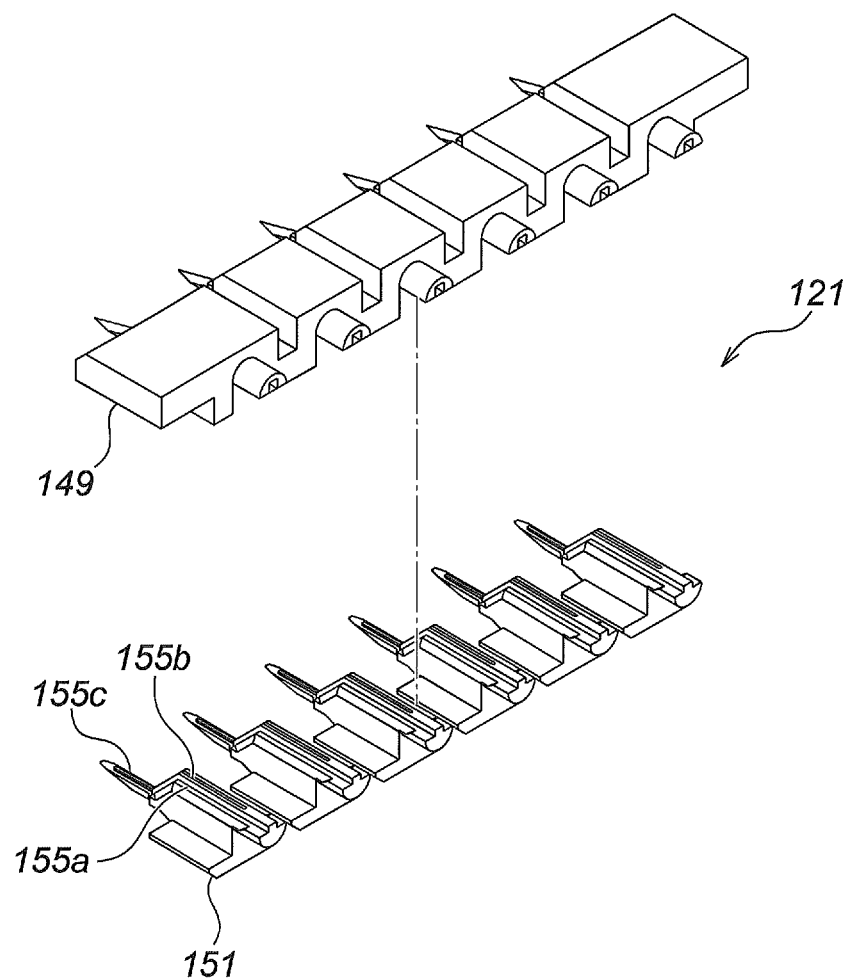
FIG. 14 An exploded perspective view of the microneedle unit of the microneedle array used for the microneedle array device according to the second embodiment of the present invention.
Figure 15:
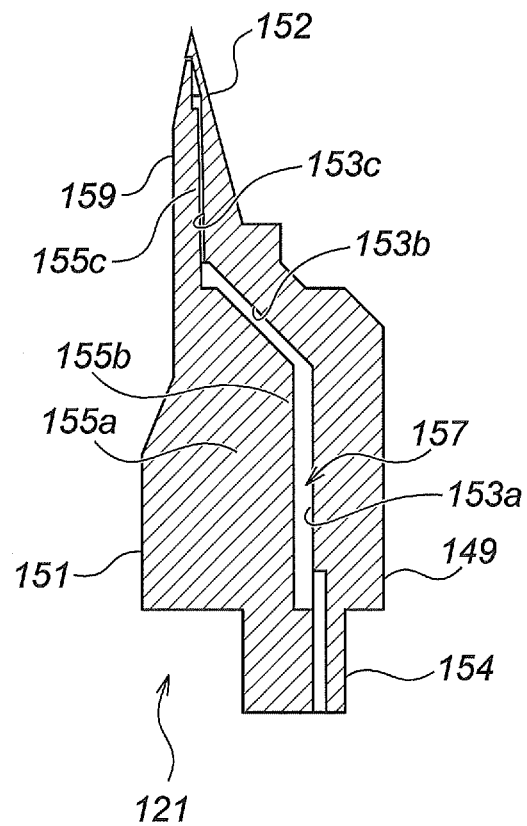
FIG. 15 A sectional view according to the second embodiment of the present invention, as viewed from the line XV-XV of FIG. 13.
Figure 16:
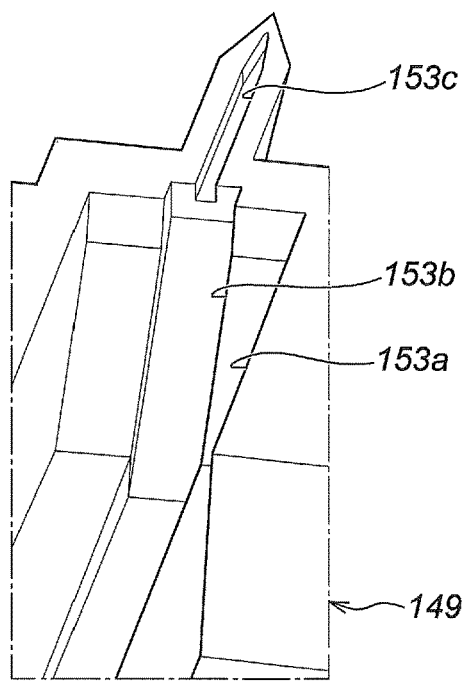
Figure 16:
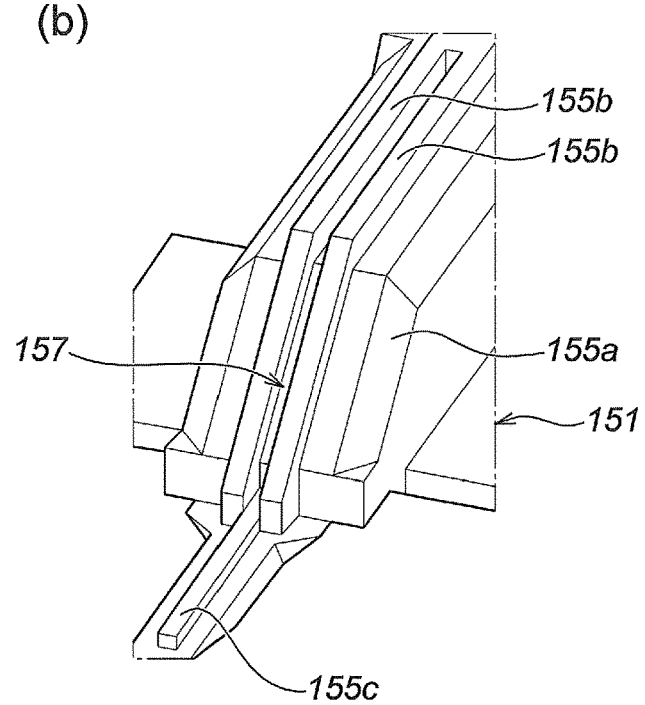

The structure of the microneedle unit 121 will now be explained. FIG. 13 through FIG. 15 illustrates the structure of the microneedle unit 121. As illustrated in FIG. 14, the microneedle unit 121 can be divided into to elements, namely a main-needle side divisional element 149 and a sub-needle side divisional element 151. The microneedle unit 121 is formed by adhering the main-needle side divisional element 149 to the sub-needle side divisional element 151. As illustrated in FIG. 13, each of the microneedle units 121 is provided with a plurality of (in the present embodiment, six) microneedles 152. Each of these six microneedle 152 has a flow channel boss 154 at the base part thereof. Each of the flow channel bosses 154 is inserted in the corresponding medicinal solution distribution hole 143 of the needle holder as discussed above, whereby the microneedle unit 121 is held by the needle holder 123.

The structure of the main-needle side divisional element 149 and the sub-needle side divisional element 151 will be discussed in detail. As illustrated in FIG. 16(a), a first engagement groove 153a is formed on the main-needle side divisional element 149, and a second engagement groove 153b is formed at the center of the first engagement groove 153a. There is a third engagement groove 153c, formed separately at the tip thereof.

On the other hand, with reference to the sub-needle side divisional element 151, a first engagement rib 155a relatively in a larger size is formed to be projecting therefrom. The first engagement rib 155a has a pair of second engagement ribs 155b, 155b, formed to be projecting therefrom. There is a third engagement rib 155c at the tip, formed separately to be projecting therefrom.

When the main-needle side divisional element 149 and the sub-needle side divisional element 151 are jointed with each other, the medicinal solution flow channel 157 is formed. To explain more particularly, the first engagement groove 153a becomes in engagement with the first engagement rib 155a. Also, the both end sides of the second engagement groove 153b become in engagement with the pair of second engagement ribs 155b, 155b. Consequently, a part of the medicinal solution flow channel 157 is formed between the pair of the second engagement ribs 155b, 155b. When the third engagement rib 155c becomes in engagement with the inner portion of the third engagement groove 153c, a space is formed between the third engagement groove 153c and the third engagement rib 155c. This space serves as the remaining part of the medicinal solution flow channel 157 as discussed above. The rear end of the medicinal solution flow channel 157 is elongating to the flow channel boss 154 as discussed above.

The tip of the microneedle 152 is free from adhesion and serve as a medicinal solution outlet, likewise the case of the first embodiment as discussed above.

As discussed above, the medicinal solution flow channel 157 is formed by engagement of the first engagement groove 153a, the second engagement groove 153b and the third engagement groove 153c, with the first engagement rib 155a, the pair of second engagement ribs 155b, 155b and the third engagement rib 155c, and accordingly, a strong joint structure between the main-needle side divisional element 149 and the sub-needle side divisional element 151 can be obtained. In addition, the tip of the sub-needle side divisional element 151 is provided with a straight part 159, and therefore the improvement of puncture performance is accomplished.

Figure 17:
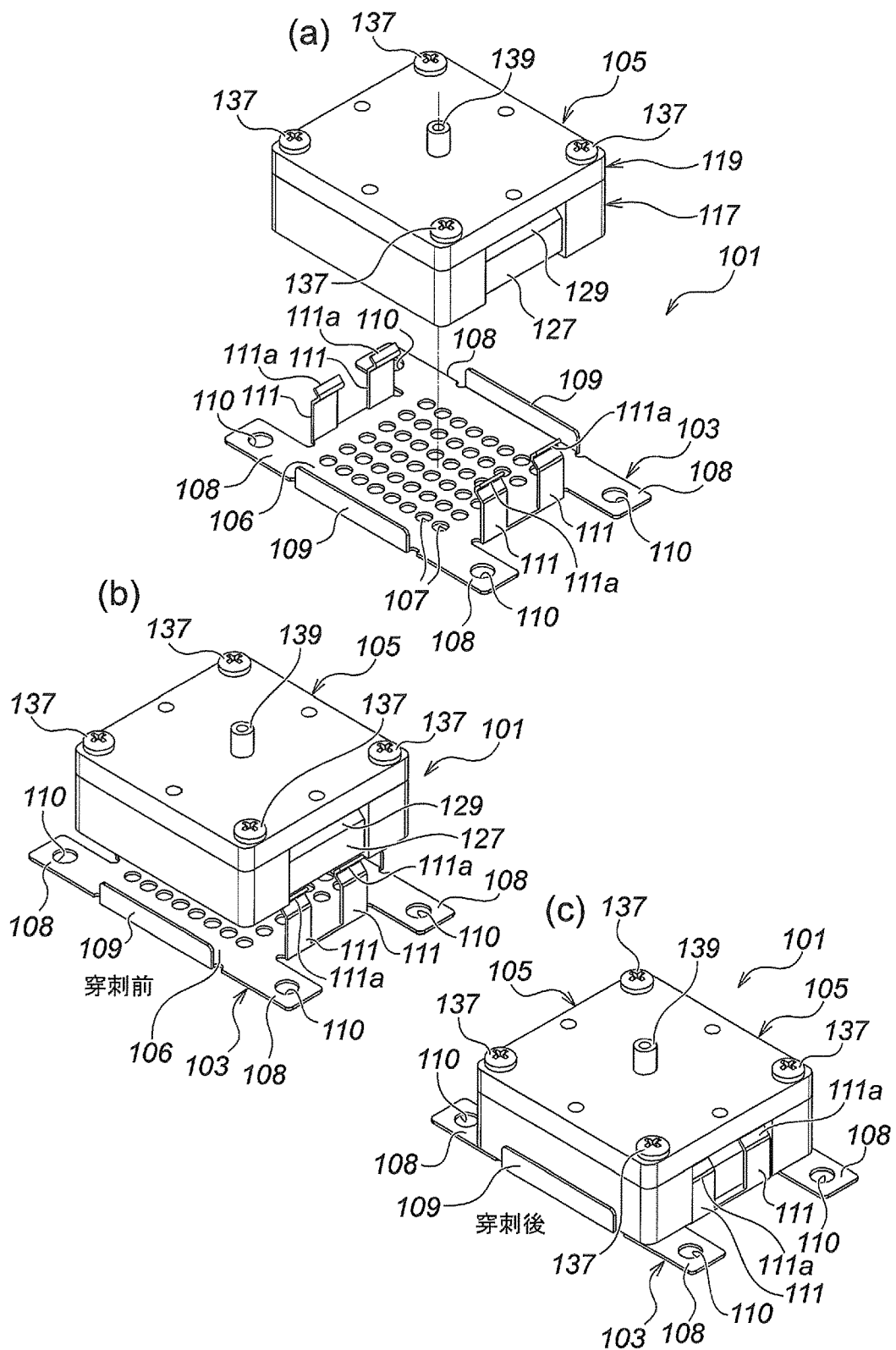

The function of the above structure will be explained with reference to FIG. 17.

The function is basically the same as that of the first embodiment as discussed above. As illustrated in FIG. 17(a), the release paper 115 is released from the jig for microneedle array placement 103, and the thus exposed adhering part 113 is adhered to and fixed on the skin surface 45.

Thereafter, as illustrated in FIG. 17(b), the microneedle array 105 is attached to the jig for microneedle array placement 103, which is adhered to and fixed on the skin surface 45. Thus, as illustrated in FIG. 17(c), the microneedle array 105 is attached to and fixed in the jig for microneedle array placement 103, and is pressed to the skin surface 45, whereby a desired puncture can be carried out. Further, by engagement of the stepped parts 129, 129 with the holding hooks 111a, 111a of the latches 111, 111, the microneedle array 105 is fixed in the jig for microneedle array placement 103. When the medicinal solution is supplied via the medicinal solution inlet 139, the medicinal solution flows into each of the microneedle units 121 via the corresponding medicinal solution distribution groove 142, and accordingly the injection under the skin surface is carried out, from each of the medicinal solution outlets at the tip of the corresponding microneedle 152, via the medicinal solution flow channel 157.

As discussed above, according to the second embodiment of the present invention, substantially the same effects as those of the first embodiment can be accomplished, and the improvement of operability is accomplished.

A test for verifying the effects of the microneedle array device 101 according to the second embodiment was performed, of which result will be discussed with reference to FIG. 18.

Figure 18:
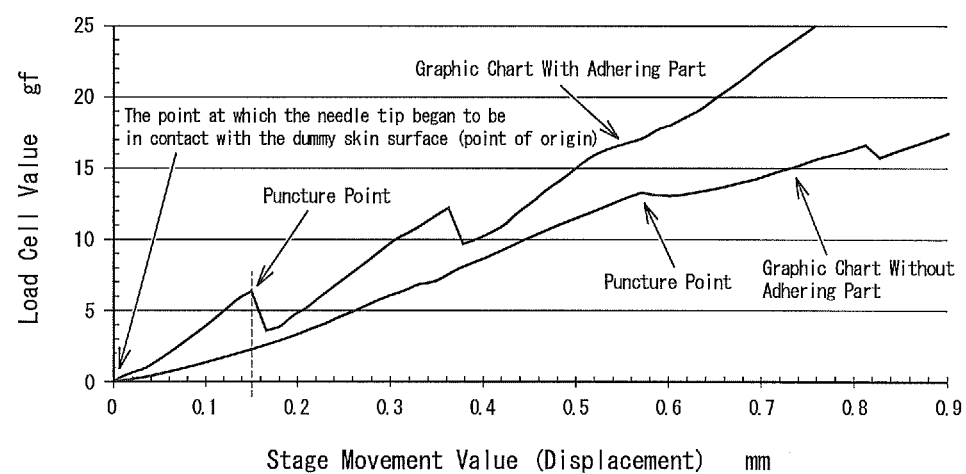
FIG. 18 A graphic chart explaining the effect of the second embodiment of the present invention.

FIG. 18 is a graphic chart, of which horizontal axis refers to a stage movement value (displacement) (mm), and of which vertical axis refers to a load cell value, whereby showing the variation in accordance with the passing of time. This experiment was carried out, by using the microneedle array device 101 according to the present embodiment, and the load when puncturing in the dummy skin surface was detected by load cell, and also the displacement value of the dummy skin surface was measured. Similarly, in the present experiment, the load and the displacement value of the dummy skin surface were also measured as a comparative example, in which the microneedle array was punctured directly into the dummy skin surface without using the jig for microneedle array placement 103. The upper line of the drawing shows the present embodiment, and the lower line shows the comparative example.

First, according to the present embodiment, after starting puncture, the load cell value increases gradually, and accordingly the pressed dummy skin surface is displaced gradually. When the dummy skin surface is displaced for about 0.175 mm, the microneedles penetrate into the dummy skin surface, and accordingly the load cell value goes down.

On the other hand, with reference to the comparative example, when the dummy skin surface is displaced for about 0.585 mm, the microneedles penetrate into the dummy skin surface. Thus the penetration timing is considerably delayed, and the load cell value is larger.

Therefore, with reference to the comparative example, the dummy skin surface is considerably deformed during puncture, and consequently, a larger force is required for carrying out a desired puncture. On the other hand, with reference to the present embodiment, the deformation of the dummy skin surface during puncture can be suppressed, and a force for carrying out a desired puncture can be minimized.

The above effect can also be accomplished in the case of the first embodiment as discussed above.

According to the graphic chart of the present embodiment, there is a point after puncture (the displacement value is about 0.33 mm), at which the load cell value goes down again. This is because of the shape of the microneedle 152, namely, the load cell value goes down at that point where the slope-shaped tip part changes to the parallel-shaped part.

The microneedle unit 121 is fixed by inserting the flow channel bosses 154 thereof into the medicinal solution distribution holes 143 of the needle holder 123, and therefore the positioning and retention can be facilitated. The positioning and retention of the microneedle unit 121 can also be carried out by the upper case 117, having the guide grooves 133, 133 formed to be opposing to those on the other side.

According to the present embodiment, with reference to the microneedle unit 121, the medicinal solution flow channel 157 is formed by jointing the main-needle side divisional element 149 with the sub-needle side divisional element 151 under the recess-and-projection engagement structure, and therefore the stiffness of the microneedle unit 121 itself can be increased. In particular, since the first engagement rib 155a of the sub-needle side divisional element 151 engages deeply into the main-needle side divisional element 149, the sufficient engagement strength is secured, and the leak out can be prevented efficiently.

A third embodiment of the present invention will now be discussed with reference to FIG. 19 through FIG. 21. According to the third embodiment, there is a microneedle array device 201, composed of a jig for microneedle array placement 203, and the detachable microneedle array 105 attached to the jig for microneedle array placement 203.

The microneedle array 105 has the same structure as that of the second embodiment of the present invention discussed above, and therefore the same reference numerals have been allotted for the same structural elements, and the detailed explanation will not be made.

Figure 19:
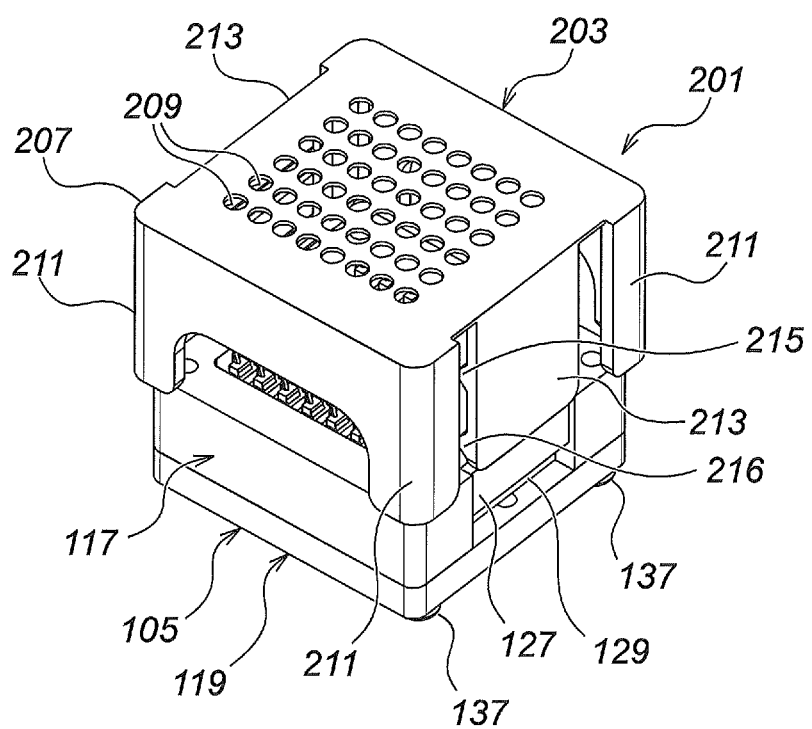
FIG. 19 A perspective view of a microneedle array device according to a third embodiment of the present invention.
Figure 20:
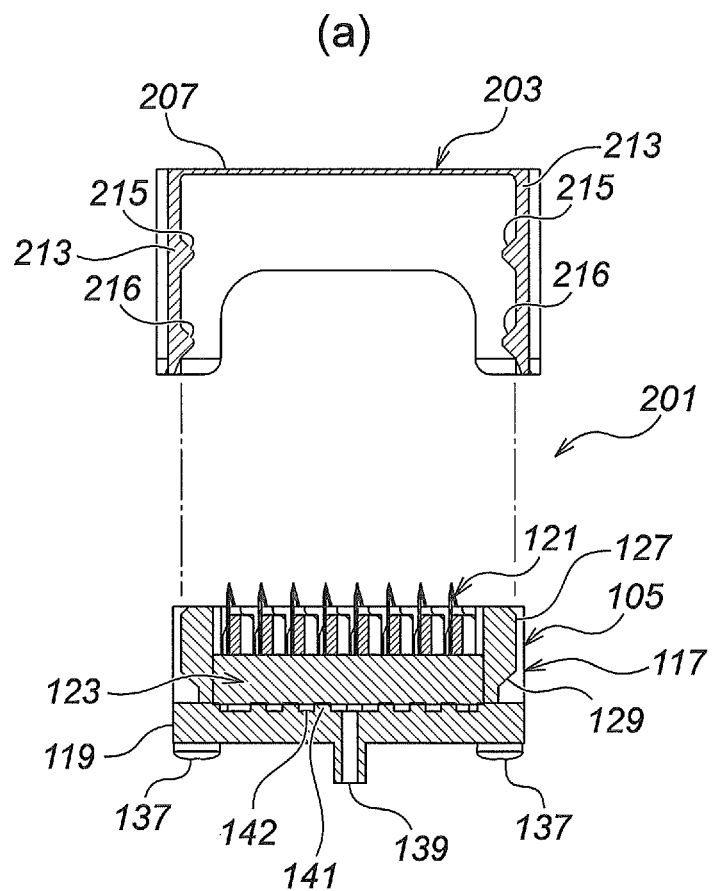
Figure 20:
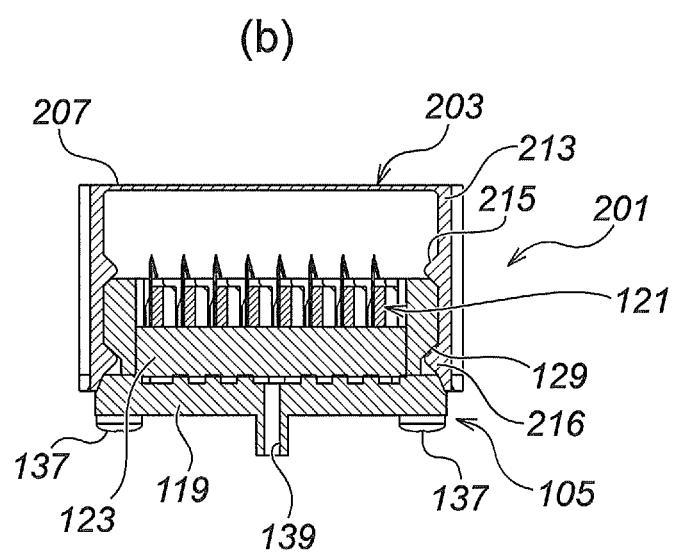

FIG. 19 is a perspective view in which the microneedle array 105 is to be attached to the jig for microneedle array placement 203.

First, the structure of the jig for microneedle array placement 203 will be explained. As also illustrated in FIG. 20, there is a main jig body 207. The main jig body 207 is substantially in a quadrilateral bucket shape, having a plurality of (in the present embodiment, 6×8=48) through holes 209 formed on the upper surface thereof. The main jig body 207 also has guiding corner walls 211 formed at the four corners thereof, respectively. The main jig body 207 is also provided with latches 213, 213, serving as microneedle array holders, on the two sides opposing to each other. As illustrated in FIG. 20(a), a first projecting part 215 and a second projecting part 216 are formed to be projecting, respectively, from the inner wall of the latch 213.

The main jig body 207 is provided with an adhering part by applying unillustrated adhesive thereto, to which an unillustrated release paper is adhered.

On the other hand, as discussed above, the structure of the microneedle array 105 is the same as that of the microneedle array 105 of the second embodiment of the present invention.

With this structure, FIG. 20(b) shows the non-use state, in which the second projecting part 216 is engaged with the stepped part 129. In this state, the tips of the microneedle units 121 are protected without being exposed to the outside.

Figure 21:
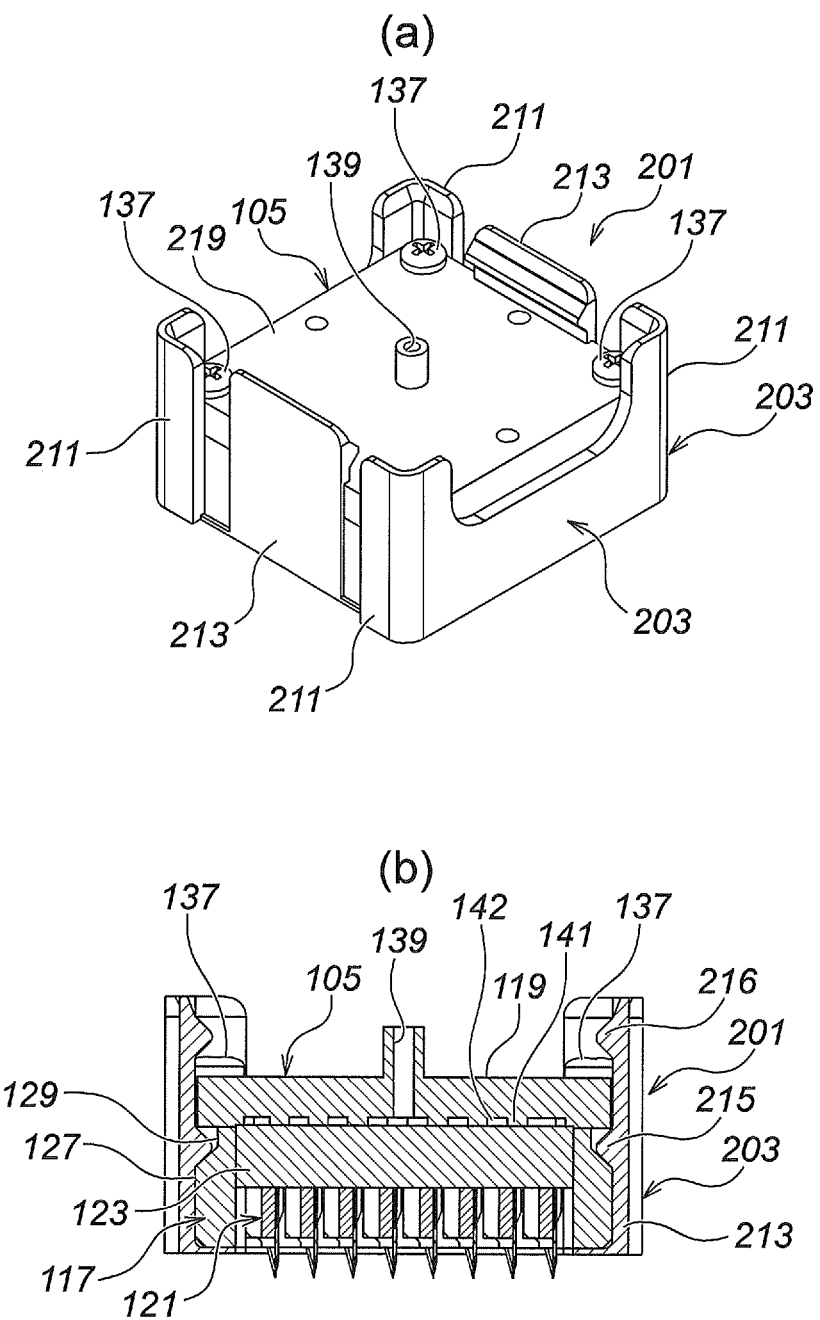

On the other hand, FIG. 21 shows the using state. In this state, as illustrated in FIG. 21(b), the first projecting part 215 is engaged with the stepped part 129.

As discussed above, according to the third embodiment of the present invention, the same effects as those of the first and second embodiments can be accomplished, and in addition, because of the engagement structure of the stepped part 129 with the first projecting part 215 as well as with the second projecting part 216, the tips of the microneedle units 121 can be protected in the non-use state, and also the penetration state can be maintained securely in the using state, whereby the improvement of operability is accomplished.

The present invention is not limited to the first through third embodiments as discussed above.

For example, according to the first through third embodiments, the adhering part is provided as an example, but the present invention is not limited to that example. For example, where the time for injection is short, it is also possible to provide a structure without having the adhering part.

For example, the number of the microneedles, and also the number of the through holes of the main jig body corresponding thereto, can be determined arbitrarily.

Further, the shape of the microneedle is not limited to the quadrangular pyramid shape, and various shapes, such as multi-sided pyramid shape or conical shape, can be utilized.

The number of the latches is not limited.

According to the first through third embodiments, the adhering part is provided in the whole area of a surface of the main jig body. However, it is also possible to provide the adhering part partially, so that the opening part of the each of the through holes may only be closed.

Further, according to the first through the third embodiments, the adhering part is provided by application of adhesive. However, it is also possible to use a double-sided adhesive paper, so that the adhering part is provided by release of a release paper on one side thereof.

The above structures are shown merely as examples, and the present invention is not limited to these structures.

INDUSTRIAL APPLICABILITY

The present invention relates to a jig for microneedle array placement and a microneedle array device. In particular, by using the jig for microneedle array placement, the deformation of the skin surface during puncture is prevented, and the microneedles can be penetrated to the prescribed depth under the skin securely. For example, the present invention is suitable for microneedle array devices used for transdermal application of insulin.

EXPLANATION OF REFERENCE SIGNS

1. Microneedle array device
3. Jig for microneedle array placement
4. Microneedle array
5. Main jig body
6. Guiding part
7. Adhering part
11. Through holes
15. latch (microneedle array holder)
29c. Microneedle

The invention claimed is:

1. A microneedle array device, comprising:
a microneedle array provided with a plurality of microneedle units, aligned in parallel such that each of the microneedle units includes a plurality of microneedles disposed in an array in a straight line;
a main jig body provided with a plurality of through holes for penetration of said microneedles; and
a guiding part for guiding said microneedle array incorporated in said main jig body, so that said microneedles are lead to said through holes,
wherein said each of the microneedle units includes a bonded structure of a pair of divisional elements halved in a longitudinal direction of said each of the microneedle units, the divisional elements including grooves disposed on the divisional elements, such that boundaries of solution channels are formed within the grooves with bonding the pair of divisional elements that face each other.

2. The microneedle array device as claimed in claim 1, wherein said main jig body is provided with microneedle array holders for holding said microneedle array incorporated in said main jig body.

3. The microneedle array device as claimed in claim 2, wherein said microneedle array holders comprise latches placed to be opposing to each other in said main jig body.

4. The microneedle array device as claimed in claim 3, wherein said main jig body is provided with microneedle array holders provided with belt connecting holes for connecting fastening belts.

5. The microneedle array device as claimed in claim 1, wherein said microneedle array comprises a plurality of microneedle units held by a needle holder, in a state of being sandwiched and fixed between an upper case, and a lower ease including a medicinal solution inlet.

6. The microneedle array device as claimed in claim 5, wherein said upper case includes the grooves formed for guiding both ends of said microneedle units.

7. The microneedle array device as claimed in claim 6, wherein said microneedle units are provided with flow channel bosses, and are fixed by inserting said flow channel bosses into through holes formed in said needle holder.

8. The microneedle array device as claimed in claim 7, wherein said lower case is provided with a plurality of projections for preventing deformation of said needle holder, and spaces between said plurality of projections serve as flow channels.

9. The microneedle array device as claimed in claim 1, further comprising:
a release paper sticking to an adhering part in a non-use state, and in a using state, said adhering part in a state of blocking said through holes of said main jig body is exposed by releasing of said release paper.

10. The microneedle array device as claimed in claim 5, wherein said needle holder holds said microneedle units in a plurality of arrays.

11. The microneedle array device as claimed in claim 5, wherein said needle holder includes an elastic body.

12. The microneedle array device as claimed in claim 5, wherein said upper case is provided with a stage part, and
wherein said main jig body includes a two-stage engagement part, comprising a projection part which is engaged with said stage part in a non-use state for protecting tips of the microneedles by prohibiting puncturing, and another projection part which is engaged with said stage part in a puncturing state for maintaining the puncturing state during puncturing.

13. The microneedle array device as claimed in claim 1, wherein said microneedle array is configured such that, in a state that said microneedle array is engaged with the through holes and is pushed, each of said microneedles breaks through an adhering part.

14. The microneedle array device as claimed in claim 1, wherein said microneedle array is configured such that, in a state that said microneedle array is engaged with the through holes and is pushed, each of said microneedles penetrates into a surface of said main jig body.

15. The microneedle array device as claimed in claim 1, wherein said microneedle array is configured such that each of said microneedles breaks through an adhering part and penetrates into a surface of said main jig body.

16. The microneedle array device as claimed in claim 1, further comprising:

a release paper sticking to an adhering part, wherein, when said release paper is released, said adhering part is exposed.

17. The microneedle array device as claimed in claim 1, wherein said main jig body includes a two-stage engagement part for a non-use state and for a puncturing state.

18. The microneedle array device as claimed in claim 1, wherein an adhering part is provided on a surface of said main jig body, in a state that said adhering part blocks said through holes, and said adhering part is penetrated by said microneedles in a using state.

\* \* \* \* \*